United States Patent
Kishi et al.

[11] Patent Number: 5,412,080
[45] Date of Patent: May 2, 1995

[54] ENTEROBACTIN COMPOUNDS

[75] Inventors: Yoshito Kishi, Belmont; Bruno Tse, Cambridge, both of Mass.

[73] Assignee: President and Fellow of Harvard College, Cambridge, Mass.

[21] Appl. No.: 111,622

[22] Filed: Aug. 25, 1993

[51] Int. Cl.$^6$ .................. C07H 15/00; C07H 17/00; C07H 17/02

[52] U.S. Cl. .................. 536/4.1; 536/17.2; 536/17.9

[58] Field of Search .................. 536/4.1, 16.8, 17.2, 536/17.9

[56] References Cited

PUBLICATIONS

Harris et al. "Coordination Chemistry of Microbial Iron Transport Compounds, 19, Stability Constants and Electrochemical Behavior of Ferric Enterobactin and Model Complexes" Journal of the American Chemical Society, Sep. 1979, vol. 101, No. 20, pp. 6097–6104.
H. W. Lee, et al., J. Org. Chem., 50:4402–4404, 1985.
M. Miller et al., Acc. Chem. Res., 26:241–249, 1993.
F. Weitl et al., J. Org. Chem. 46:5234–5237, 1981.
M. Kappel, et al., Inorg. Chem. 24:2447–2452, 1985.

Primary Examiner—Nathan M. Nutter
Attorney, Agent, or Firm—Fish & Richardson

[57] ABSTRACT

Enterobactin analogs prepared from scyllo-inositol mono-orthoformate and having the following formula:

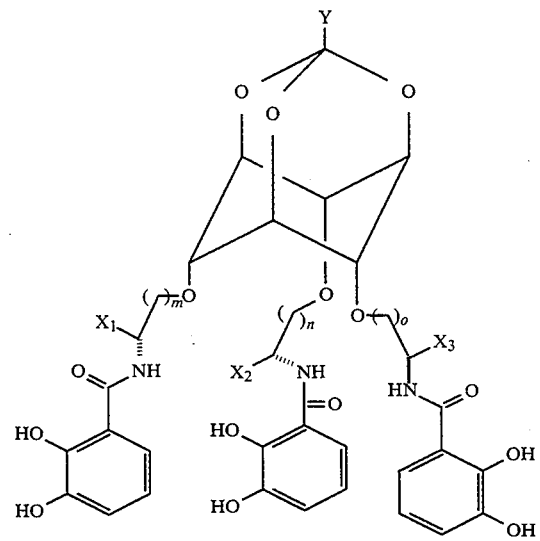

wherein each $X_1$, $X_2$ and $X_3$, independently, is H, $C_{1-20}$ alkyl, phenyl, naphthyl, $C_{7-20}$ aralkyl, or $C_{7-20}$ alkaryl; Y is H, $C_{1-20}$ alkyl, phenyl, naphthyl; $C_{7-20}$ aralkyl, $C_{7-20}$ alkaryl; —$(C_pH_{2p})$—CH$_2$OH, —$(C_pH_{2p})$—COOH or its salt, —$(C_pH_{2p})$—NR$_1$.R$_2$ or its salt, or —$(C_pH_{2p})$—N$^+$R$_1$.R$_2$.R$_3$; in which p is 1–20 and each R$_1$, R$_2$ and R$_3$, independently, is H or $C_{1-5}$ alkyl; and m, n and o, independently, is 1–6; or the enantiomer thereof.

16 Claims, 1 Drawing Sheet

ENTEROBACTIN COMPOUNDS

STATEMENT AS TO FEDERALLY SPONSORED RESEARCH

This invention was made with support from the National Institutes of Health (NS-12108) and the National Science Foundation (CHE 89-09762). Accordingly, the U.S. government has certain rights in the invention.

BACKGROUND OF THE INVENTION

Enterobactin is a siderophore produced by enteric bacteria to trap ferric ions under iron-deficient conditions and has the following structure:

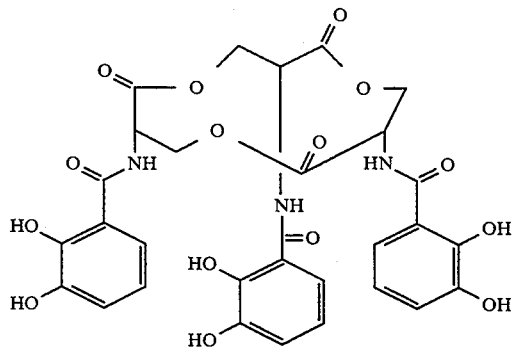

Enterobactin exhibits unique chemical properties including (1) the extraordinarily high affinity for ferric ions (stability constant ($K_f$) of ferric enterobactin being $\sim 10^{49}$) and (2) the chirality at the metal center with the exclusively right-handed ($\Lambda$) configuration. The unnatural antipode of enterobactin was shown to lack biological activities, suggesting that the chirality at the metal center plays an important role.

There have been substantial efforts in synthesizing enterobactin analogs. In particular, enterobactin analogs with enhanced lipophilicity may affect the tissue distribution of the metal complex and will have various medical applications.

SUMMARY OF THE INVENTION

One aspect of the present invention relates to novel compounds of the following formula:

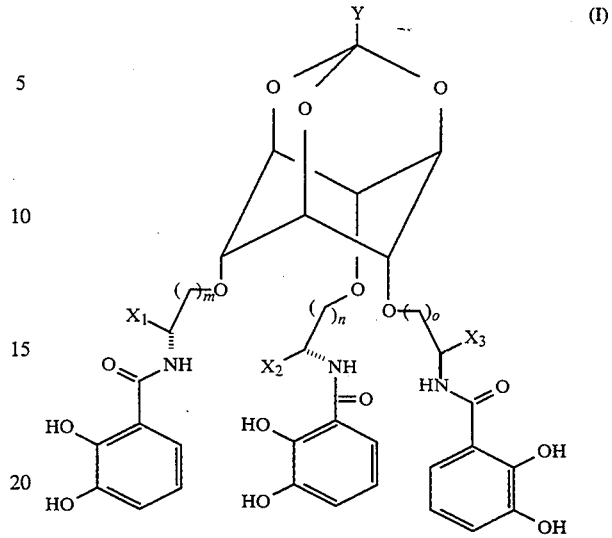

wherein each $X_1$, $X_2$ and $X_3$, independently, is H, $C_{1-20}$ alkyl, phenyl, naphthyl, $C_{7-20}$ aralkyl, or $C_{7-20}$ alkaryl;

Y is H, $C_{1-20}$ alkyl, phenyl, naphthyl; $C_{7-20}$ aralkyl, $C_{7-20}$ alkaryl; —$(C_pH_{2p})$—$CH_2OH$, —$(C_pH_{2p})$—COOH or its salt, —$(C_pH_{2p})$—$NR_1.R_2$ or its salt, or —$(C_pH_{2p})$—$N^+R_1.R_2.R_3$; in which p is 1-20 and each $R_1$, $R_2$ and $R_3$, independently, is H or $C_{1-5}$ alkyl; and m, n and o, independently, is 1-6; or the enantiomer thereof.

Note that the symbol —$(C_pH_{2p})$— above denotes an aliphatic chain, which can be either straight, i.e., —$(CH_2)_p$—, or branched.

Preferably, each $X_1$, $X_2$ and $X_3$, independently, is H, methyl, or phenyl in the compound covered by formula (I). It is also preferred that Y be H, —$CH.(CH_3)_2$, —$C(CH_3)_3$, —$(CH_2)_p$—$CH_2OH$, —$(CH_2)_p$—COOH or its salt, —$(CH_2)_p$—$NR_1.R_2$ or its salt, —$(CH_2)_p$—$N^+R_1.R_2.R_3$; or —$(CH_2)_q$—$CH_3$, in which each p and q, independently, is 1-10. Other preferred compounds include those in which m, n and o are identical, or $X_1$, $X_2$ and $X_3$ are identical, or both.

Compounds encompassed by formula (I) with each of the hydroxyl groups of the catechol moieties being blocked by an alcohol protecting group are also within the present invention. Such compounds are useful intermediates when enterobactin analogs of this invention are to be linked to proper substrates (see discussion below). Alcohol protecting groups include, but are not limited to, $R_4$—O—, $R_4$—CO—O—, $R_4$—O—CO—O—, or

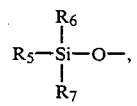

$C_{1-10}$ alkyl, $C_{2-10}$ alkenyl, $C_{2-10}$ alkynyl, $C_{7-20}$ aralkyl, $C_{7-20}$ alkaryl, phenyl or tetrahydropyranyl, and each of $R_5$, $R_6$ and $R_7$ is $C_{1-6}$ alkyl, $C_{2-6}$ alkenyl or phenyl. Note that the oxygen at the right end of the above listed alcohol protecting groups refers to the same oxygen in an —OH which is intended to be protected.

Below are some examples of alcohol protecting groups: benzyl ("Bn"), p-methoxyphenylmethyl (MePhCH$_2$O—),

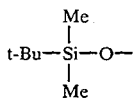

acetyl and pivaloyl.

For more details relating to alcohol protecting groups, see Chapters 2 and 3 in T. W. Greene and P. G. M. Wuts *Protective Groups in Organic Synthesis*, 2nd Ed. (1991), John Wiley & Sons, Inc., New York, which is hereby incorporated by reference.

Another aspect of the present invention relates to a composition which includes a substrate (i.e., solid phase) and an enterobactin analog. The enterobactin analog is linked to the substrate and has the following formula:

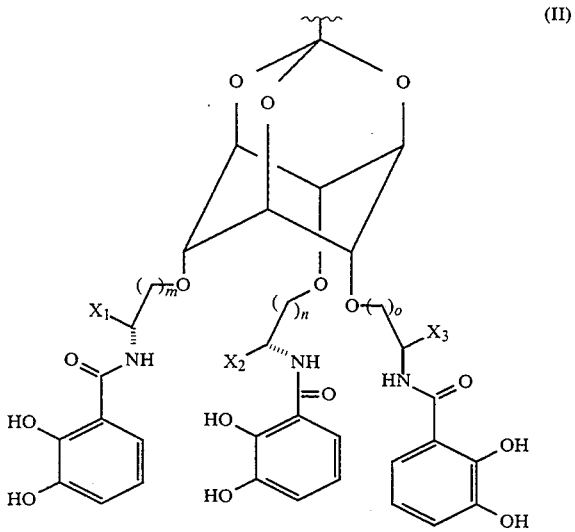

(II)

wherein each $X_1$, $X_2$ and $X_3$, independently, is H, $C_{1-20}$ alkyl, phenyl, naphthyl, $C_{7-20}$ aralkyl, or $C_{7-20}$ alkaryl; and m, n and o, independently, is 1–6; or the enantiomer thereof.

Note that in this disclosure a wavy line shown at one end of a chemical group, e.g., formula (II) above, denotes that that chemical group is to be attached to another chemical group.

Preferably, in formula (II) each $X_1$, $X_2$ and $X_3$, independently, is H, methyl, or phenyl and Y is H, —CH.(CH$_3$)$_2$, —C(CH$_3$)$_3$, —(CH$_2$)$_p$—CH$_2$OH, —(CH$_2$)$_p$—COOH or its salt, —(CH$_2$)$_p$—NR$_1$.R$_2$ or its salt, —(CH$_2$)$_p$—N$^+$R$_1$.R$_2$.R$_3$; or —(CH$_2$)$_q$—CH$_3$, in which each p and q, independently, is 1–10. It is also preferred that each m, n and o, independently, be 1.

The substrate of the above-described composition can be any inert material such as polymer (e.g., polystyrene) or glass onto which enterobactin analogs can be linked, either covalently (e.g., via an ether functionality) or noncovalently (e.g., via electrostatic force). It is desirable to provide a spacer (e.g., an aliphatic chain) between the substrate and the enterobactin linked thereto. An example of a proper aliphatic chain as spacer is —(CH$_2$)$_n$— in which n is 10–20.

Other features and advantages of the present invention will be apparent from the following drawing and description of the preferred embodiments, and also from the appending claims.

BRIEF DESCRIPTION OF THE DRAWING

The drawing is first described.

DESCRIPTION OF THE PREFERRED EMBODIMENTS

Figure 1:
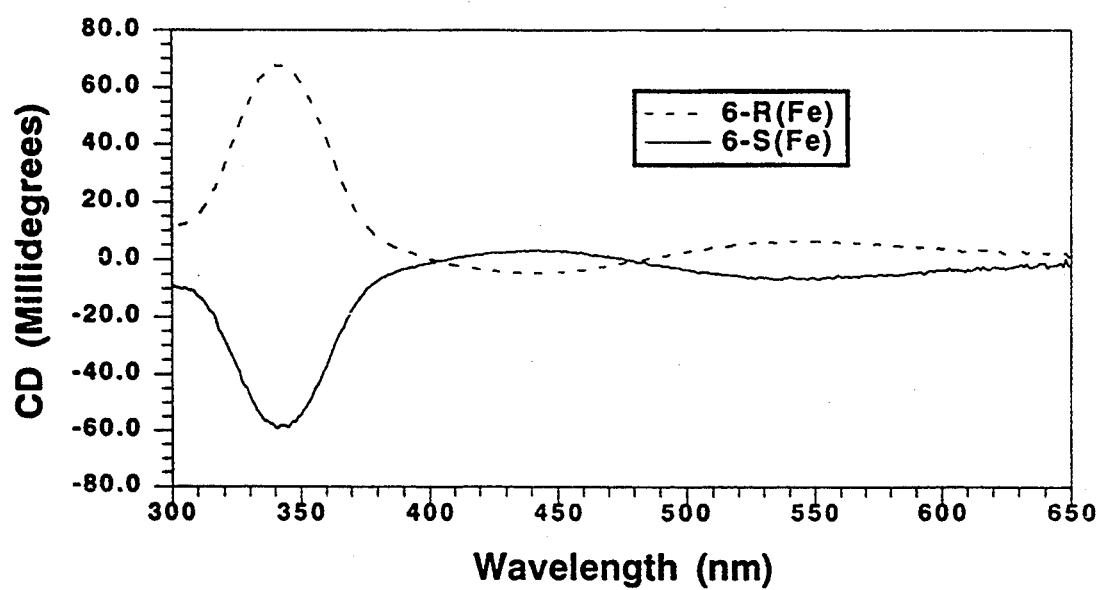
FIG. 1 is a CD spectra of ferric complexes of two enterobactin analogs of this invention, 6-R and 6-S, recorded at 10$^{-4}$M concentration in a 1:1 mixture of MeOH and 0.01M phosphate buffer (pH 7.0).

This invention teaches preparation of enterobactin analogs based on the unique structure of scyllo-inositol mono-orthoformate, which has three hydroxyl groups axially disposed at the 1, 3, and 5 positions of the cyclohexane ring. For example, scyllo-inositol mono-orthoformate has two appealing structural features for the design of enterobactin analogs: (1) a chiral ligand can be attached to each of the three hydroxyl groups, and the resulting compound forms a complex with chirality at the metal center; and (2) the orthoformate group can be replaced by other orthoesters, which allows tuning of the polarity of the metal complexes.

Referring now to formula (I) shown above, the modifications of chemical/physical properties of the enterobactin analogs of this invention include both changing the substitutent (i.e., $X_1$, $X_2$ or $X_3$) or the length of the side chain (i.e., m, n or o) in the moiety attached to one of the hydroxyl groups of the basic scyllo-inositol mono-orthoformate structure, and tuning its orthoester moiety (i.e., Y). Such modifications give diverse enterobactin analogs which differ in their lipophilicity/hydrophilicity and capability to bind various metal ions. Also, introduction of a proper functionality (e.g., hydroxyl, carboxyl or ammonium) in the Y moiety enables one to link the enterobactin analog to a proper substrate.

The enterobactin analogs of the present invention can be used for limiting microbial growth, imaging abscesses and tumor, delivering drug or treating iron overload. See Weitl, F. L.; Raymond, K. N. *J. Org. Chem.*, 46:5234 (1981); Kappel, M. J.; Pecoraro, V. L.; Raymond, K. N. *Inorg. Chem.*, 24:2447 (1985); and Miller, M. J.; Malouin, F. *Acc. Chem. Res.* 26:241 (1993); all of which are hereby incorporated by reference. The enterobactin analogs of this invention can also be immobilized onto a solid phase (e.g., polystyrene) for removal of metal ions from a liquid, such as waste solutions produced by a factory or plant.

The specific working examples set forth below are to be construed as merely illustrative, and not limitative of the remainder of the disclosure in any way whatsoever. The structures of the enterobactin analogs (R enantiomer) of this invention synthesized in Examples 1–7 below are as follows:

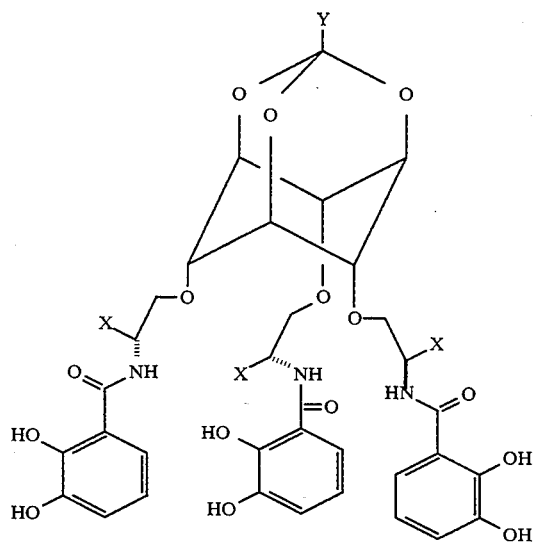

6-R: X=Ph and Y=H
6-S: the enantiomer of 6-R
7: X =H and Y =H
10-R: X=Ph and Y=C$_{10}$H$_{21}$
10-S: the enantiomer of 10-R
11-R: X=Me and Y=H
11-S: the enantiomer of 11-R EXAMPLE 1: Synthesis of 6-R 6-R was prepared from scyllo-inositol mono-orthoformate by the following procedures. For synthesis of scyllo-inositol mono-orthoformate, see Lee, H. W.; Kishi, Y. *J. Org. Chem.*, 50:4402 (1985), which is hereby incorporated by reference.

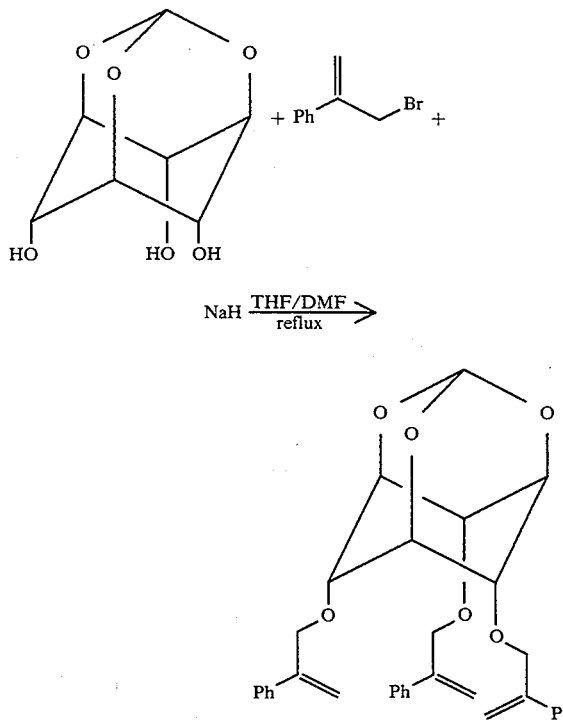

The triol (500 mg, 2.63 mmol) was dissolved in 10 ml of dry DMF. 3-Bromo-2-phenyl-1-propene (15.7 g, 79.7 mmol; prepared by the literature procedure (Hatch, L. F.; Patton, T. L. *J. Am. Chem. Soc.*, 76:2705 [1954]) in 40 ml anhydrous THF was then added, followed by NaH (60% mineral oil dispersion; 2 g, 50 mmol). The mixture was then refluxed under argon overnight. The mixture was cooled to room temperature. The excess NaH was quenched with the addition of crushed ice. 100 ml of water was then added, and the product was extracted with CH$_2$Cl$_2$ three times (150 ml each). The combined organic fraction was dried over Na$_2$SO$_4$ and filtered. The solvent was removed under reduced pressure. After flash chromatography, 1.19 g of product was obtained (84% yield).

MS (FAB): m/z=561 (M+Na), 329, 307, 289, 233, 219, 199.

HRMS: calcd=561.2253 (M+Na); found =561.2271.

IR (film): 2923 cm$^{-1}$, 1631, 1496, 1446, 1355, 1166, 1131, 1079, 1002, 943, 911, 779, 699.

UV (CH$_2$Cl$_2$): $\lambda_{max}$ 243 nm ($\epsilon$25,300).

$^1$H NMR (CDCl$_3$): 4.24 ppm (3H, dd, J=2.69 Hz, 4.21),4.32 (3H, dd, J=2.69 Hz, 4.21), 4.36 (6H, broad), 5.30 (3H, broad), 5.45 (1H, s), 5.48 (3H, broad), 7.22–7.46 (15H, m).

$^{13}$C NMR (CDCl$_3$): 68.7 ppm, 71.1, 71.8, 103.2, 114.7, 126.3, 127.7, 128.3, 144.0, 151.6.

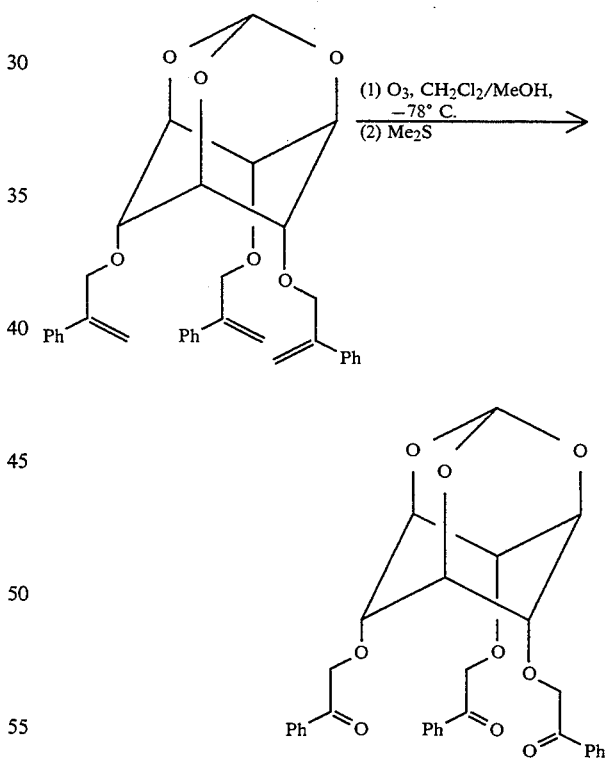

The starting material (763 mg, 1.42 mmol) was dissolved in 30 ml of CH$_2$Cl$_2$ and 60 ml of methanol. Ozone gas was then blown through the mixture at −78° C. until a blue colour persisted (approximately 10 minutes). Nitrogen gas was then blown through the mixture to remove the excess ozone. Me$_2$S (30 ml) was then added. The mixture was then stirred at −78° C. for half an hour, and at room temperature for another half an hour. The mixture was concentrated in vacuo. After column chromatography, 710 mg of the triketone was obtained (92% yield).

MS (FAB): 567 (M+Na), 447, 360, 329, 307.
HRMS: calcd =567.1631 (M+Na); found =567.1617.
IR (film):3064 cm$^{-1}$ 2923, 1759, 1699, 1597, 1581, 1449, 1401, 1364, 1290, 1230, 1163, 1096, 1044, 999, 940, 836, 756, 690, 671, 602.
UV (CH$_2$Cl$_2$): $\lambda_{max}$ 280 nm (2,800), 243 (29,720).
$^1$H NMR (CDCl$_3$):4.36 ppm (3H, dd, J=2.8 Hz, 4.4), 4.77 (3H, dd, J=2.8 Hz, 4.4), 4.90 (6H, s), 5.48 (1H, s), 7.35–7.95 (15H, m).
$_{13}$C NMR (CDCl$_3$): 68.5 ppm, 72.7, 73.7, 103.0, 128.2, 128.6, 133.5, 151.6, 196.2.

MS (FAB): m/z =573 (M+Na).
HRMS: calcd =573.2100 (M+Na); found =573.2086.
IR (film): 3446 cm$^{-1}$ 3087, 3061, 3031, 2962, 2921, 2870, 1955, 1816, 1734, 1605, 1495, 1480, 1453, 1403, 1336, 1261, 1199, 1164, 1090, 1023, 943, 912, 800, 761, 701, 682, 636.
UV (CH$_2$Cl$_2$): $\lambda_{max}$ 259 nm ($\epsilon$20,240), 254 (28,600), 247 (2,880), 243 (14,300), 237 (8,360).
$^1$H NMR (CDCl$_3$): 3.62 ppm (3H, dd, J=9.5 Hz, 9.7),3.92 (3H, dd, J=2.2 Hz, 9.5), 4.35 (3H, broad), 4.56 (3H, broad), 4.66 (3H, broad), 4.99 (3H, br d, J=2.2 Hz, 9.7), 5.52 (1H, s), 7.26–7.44 (15H, m).
$^{13}$C NMR (CDCl$_3$): 67.7ppm, 72.5, 73.8, 76.9, 102.8, 126.2, 127.9, 128.4, 139.3.
$[\alpha]_D$ +129° (CH$_2$Cl$_2$).

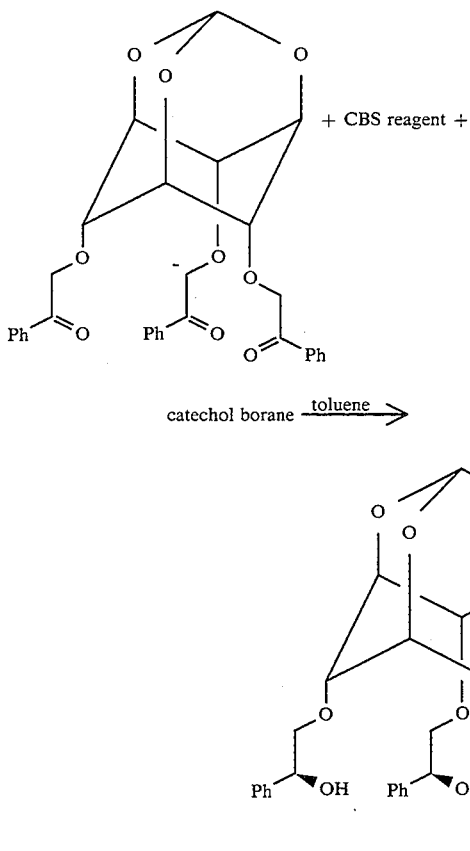

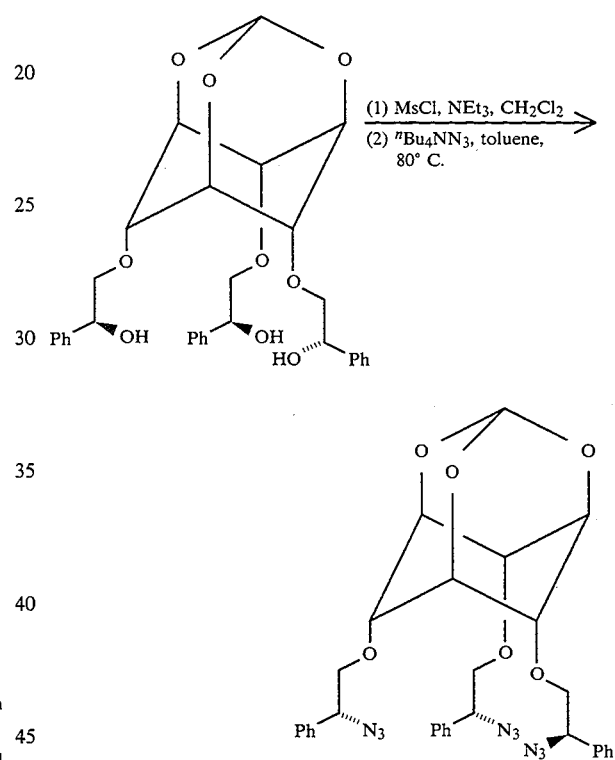

The triketone (71.4 mg, 0,131 mmol) was dissolved in 7 ml of anhydrous toluene, The CBS reagent (prepared from (s)-α,α-diphenyl-2-pyrrolidimemethanol according the literature procedure (Cory, E. J.; Bakshi, R. K.; Shibata, S., J. Am. Chem. Soc., 109:5551 [1987], hereby incorporated by reference); 1.3 ml of 0.2M solution in toluene, 0.26 mmol) was then added. The mixture was stirred at −78° C. Catechol borane (0.2 ml, 1.88 mmol) in 7 ml of anhydrous toluene was added to the mixture over half an hour at −78° C. Stirring was continued at −78° C. for three more hours, then at room temperature overnight. 1N NaOH (10 ml) was then slowly added at 0° C. The mixture was stirred for half an hour until a black color was obtained. The product was then extracted with CH$_2$Cl$_2$ four times (50 ml each). The combined organic fraction was dried over Na$_2$SO$_4$, and filtered. The solvent was removed under reduced pressure. After column chromatography, 72.5 mg of crude triol product was obtained, which was directly used in the next step. The assignment of the configuration is based on the literature precedent for the CBS reduction. The analytical sample was obtained by preparative tlc purification.

The crude triol obtained above (72.5 mg, 0.132 mmol) was dissolved in 15 ml of anhydrous CH$_2$Cl$_2$. Triethylamine (0.17 ml, 1.22 mmol) was then added, and the mixture was stirred at 0° C. Methanesulfonyl chloride (0.062 ml, 0.780 mmol) was then added. Stirring was continued at 0° C. and the mixture was allowed to warm up to room temperature over an hour. 100 ml of ether was then added, and the organic layer was washed with saturated NaHCO$_3$ solution, water, and finally with brine. The organic fraction was then dried over Na$_2$SO$_4$, and filtered. The solvent was then removed under reduced pressure, and the crude trimesylate obtained was used directly in the next step without further purification.

The trimesylate obtained above was dissolved in 15 ml of anhydrous toluene and tetrabutylammonium azide (approximately 2 g, 7.04 mmol) was then added, and the mixture was stirred at 80° C. overnight. The solvent was removed under reduced pressure. After column chromatography, 52.4 mg of triazide was obtained (64% yield over 3 steps).

MP (CH$_2$Cl$_2$/hexane): 122°–124° C.
MS (FAB): m/z=648 (M+Na).
HRMS: calcd=648.2295 (M+Na); found=648.2288.
IR (film): 2924 cm$^{-1}$, 2885 2136 2101 1495, 1451, 1346, 1315, 1288, 1255, 1159, 1144, 1082, 1065, 1027, 993, 963, 939, 858, 756, 703, 697, 650, 610.
UV (CHCl$_3$): λ$_{max}$ 264 nm (ε1,090), 257 (1,180), 252 (970), 240 (820).
$^1$H NMR (CDCl$_3$): 3.64 ppm (3H, dd, J=8.64 Hz, 9.97), 3.92 (3H, dd, J=3.89 Hz, 9.97), 4.26 (3H, broad), 4.46 (3H, broad), 4.72 (3H, dd, J=3.63Hz, 8.64), 5.48 (1H, s), 7.30–7.38 (15H, m).
$^{13}$CNMR (CDCl$_3$): 65.31 ppm, 68.22, 73.86, 73.93, 102.98, 127.04, 128.52, 128.77, 136.44.
[α $_D$ −54°.

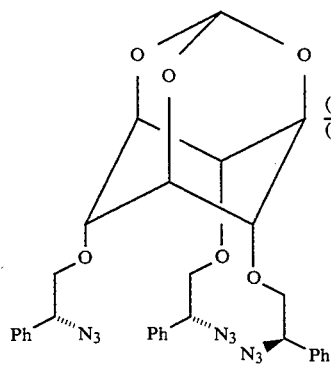

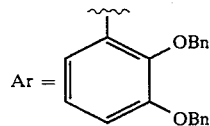

The triazide (10.1 mg, 0.0162 mmol) was dissolved in 1.5 ml of THF and 3 ml of methanol. Pearlman's catalyst (15 mg) was added. The mixture was then stirred under a hydrogen atmosphere (balloon) for 90 minutes, and filtered through a tightly packed cotton wool in a disposable pipette with thorough rinsing with THF/MeOH. The filtrate was then concentrated in vacuo to give 9 mg of the crude triamine which was used in the next step without further purification.

The triamine thus obtained was dissolved in 4 ml of anhydrous CH$_2$Cl$_2$. The dibenzylated 2,3-dihydroxybenzoic acid (21.4 mg, 0,064 mmol), DCC (13.2 mg, 0,064 mmol) and HOBt (8.65 mg, 0.064 mmol) were added. The mixture was stirred at room temperature under argon overnight. The precipitated urea was filtered off and rinsed with cold CH$_2$Cl$_2$. The filtrate was concentrated in vacuo and purified by preparative tlc, to give the product (16.9 mg, 70% yield over 2 steps).
MS (FAB): m/z=1519 (M+Na).
HRMS; calcd=1518.5878 (M+Na); found=1518.5814.
IR (film): 3370 cm$^{-1}$ 3062, 3032, 2929, 2870, 1658, 1576, 1515, 1497, 1454, 1373, 1313, 1265, 1212, 1166, 1084, 1028, 1001, 945, 913, 853, 807, 754, 698, 636.
UV (CH$_2$Cl$_2$): λ$_{max}$ 293 nm (ε5,120), 260 (28,800), 255 (42,300), 248 (40,400), 243 (34,600), 237 (32.,700), 228 (37,800).
$^1$H NMR (CDCl$_3$): 3.26 ppm (3H, dd, J=6.7 Hz, 10.3), 3.38 (3H, dd, J=6.3Hz, 10.3), 3.89 (3H, dd, J=2.7Hz, 4.0), 4.04 (3H, dd, J=2.7Hz, 4.0), 4.90 (6H, AB, J=10.5Hz), 5.04 (6H, s), 5.11 (3H, ddd, J=6.3Hz, 6.7, 7.6), 5.35 (1H, s), 7.00–8.10 (54H, m).
$^{13}$C NMR (CDCl$_3$): 52.75 ppm, 68.25, 70.80, 71.24, 72.73, 75.94, 102.91, 116.79, 123.18, 124.31, 127.38, 127.69, 127.90, 128.19, 128.36, 128.42, 128.44, 128.52, 128.62, 136.34, 136.42, 139.48, 146.59, 151.74, 164,56.
[α $_D$ +17°.

The dibenzylated 2,3-dihydroxybenzoic acid used in the above reaction was prepared by the following procedure:

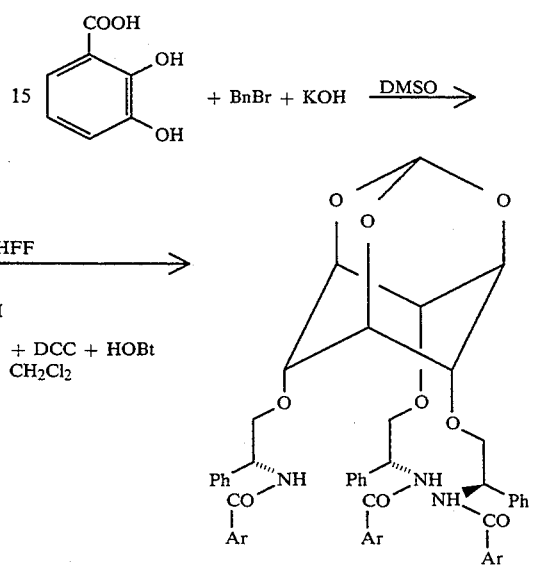

To a mixture of 2,3-dihydroxybenzoic acid (2.0 g, 13.0. mmol) and powdered potassium hydroxide (8.74 g, 155 mmol) was added 40 ml of DMSO. The mixture was stirred under argon at room temperature. Benzyl bromide (7.7 ml, 64.8 mmol) was then added, and the reaction mixture was stirred for four hours. 20 ml of water was then added, and the mixture was stirred for another two hours. The mixture was then acidified with 1N HCl and the product was extracted with ethyl acetate. The organic fraction was washed two times with water and then dried over Na$_2$SO$_4$, and filtered. The solvent was removed under reduced pressure. Recrystallization from CH$_2$Cl$_2$/hexane gave 3.85 g of the dibenzylated product MP (CH$_2$Cl$_2$/hexane): 125°–126° C.
MS (FAB): 357(M+Na), 329, 307, 289, 273, 257, 235, 219, 199.
HRMS: calcd=357.1103(M+Na); found=357.1094.
IR (film): 3063 cm$^{-1}$ 3032, 2945, 2875, 2678, 2576, 1922, 1809, 1692, 1598, 1577, 1498, 1474, 1455, 1416, 1377,

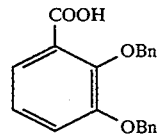

1313, 1261, 1237, 1219, 1199, 1160, 1090, 1036, 1027, 1004, 966, 915, 902, 863, 844, 822, 814, 767, 751, 734, 698, 662, 613.

UV (CH$_2$Cl$_2$): λ$_{max}$ 300 (ε3,930), 261 (1,890), 255 (2,360), 248 (3,690), 244 (5,970), 229 (11,710).

$^1$H NMR (CDCl$_3$): 5.09 ppm (2H, s), 5.16 (2H, s), 7.05–7.65 (13H, m), 11.36 (1H, broad).

$^{13}$C NMR (CDCl$_3$=): 71.59 ppm, 77.06, 119.09, 123.17, 124.46, 124.93, 127.73, 128.48, 128.77, 129.20, 134.77, 135.89, 147.23, 151.39, 165.30.

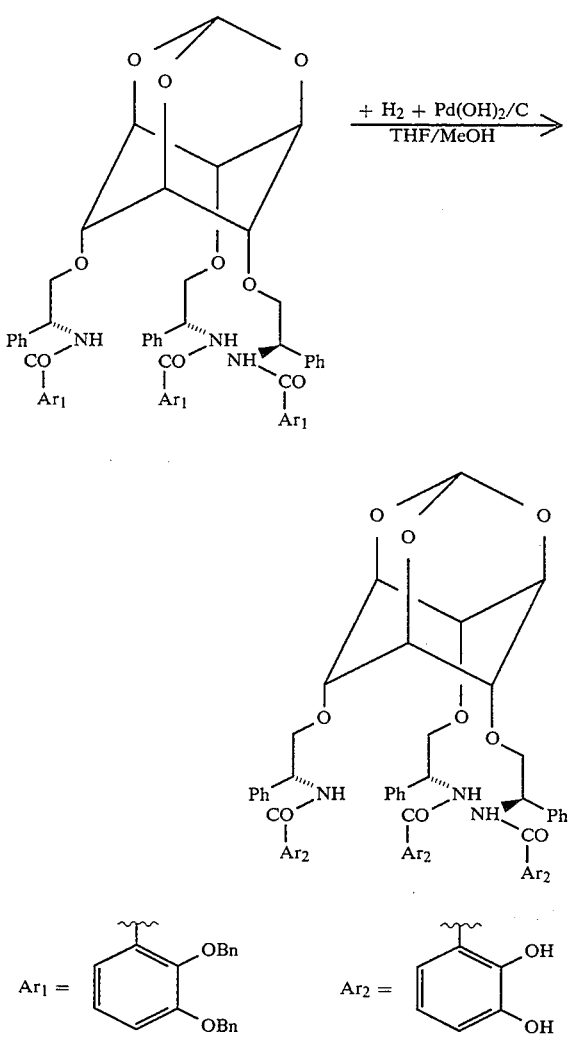

The benzylated compound (23.9 mg, 0.016 mmol) was dissolved in 3 ml of THF and 6 ml of methanol. Pearlman's catalyst (20 mg) was added. The mixture was stirred under a hydrogen atmosphere (balloon) for 90 min, and was then filtered through a piece of tightly packed cotton wool in a disposable pipette which was then thoroughly rinsed with methanol. The filtrate was concentrated in vacuo to give 14.8 mg of the product (97% yield).

MS (FAB): m/z=978(M+Na), 482, 329, 307, 225.
HRMS: calcd=978.3061(M+Na); found=978.3032.
IR (film): 3400 cm$^{-1}$ (very broad), 2925, 1641, 1586, 1529, 1494, 1455, 1331, 1267, 1163, 1081, 1011, 943, 848, 748, 699, 600.
UV (MeOH) λ$_{max}$ 315 nm (ε10,600), 250 (28,600), 209 (91,100).

$^1$H NMR (CD$_3$OD): 3.68 ppm (3H, dd, J=7.4 Hz, 10.3), 3.95 (3H, dd, J=4.9 Hz, 10.3), 4.21 (3H, dd, J=2.8 Hz, 4.0), 4.36 (3H, dd, J=2.8 Hz, 4.0), 5.25 (3H, dd, 7.4), 5.39 (1H, s), 6.72 (3H, dd, J=7.9 Hz, 8.1), 6.92 (3H, dd, J=1.4 Hz, 7.9), 7.15–7.20 (15H, m), 7.35 (3H, dd, J=1.4 Hz, 8.1).

$^{13}$C NMR (CD$_3$OD): 54.73 ppm, 69.64, 73.16, 75.26, 104.21, 117.05, 119.11, 119.90, 119.95, 127.97, 128.48, 129.49, 140.71, 147.38, 150.11, 170.85.
[α]$_D$ −40°.

EXAMPLE 2: Synthesis of 6-S

6-S (α$_D$+40°) was obtained by following the same procedures set forth in Example 1 except that Corey's (R)-CBS reagent was used instead.

EXAMPLE 3: Synthesis of 7

7 was prepared by the reactions set forth below:

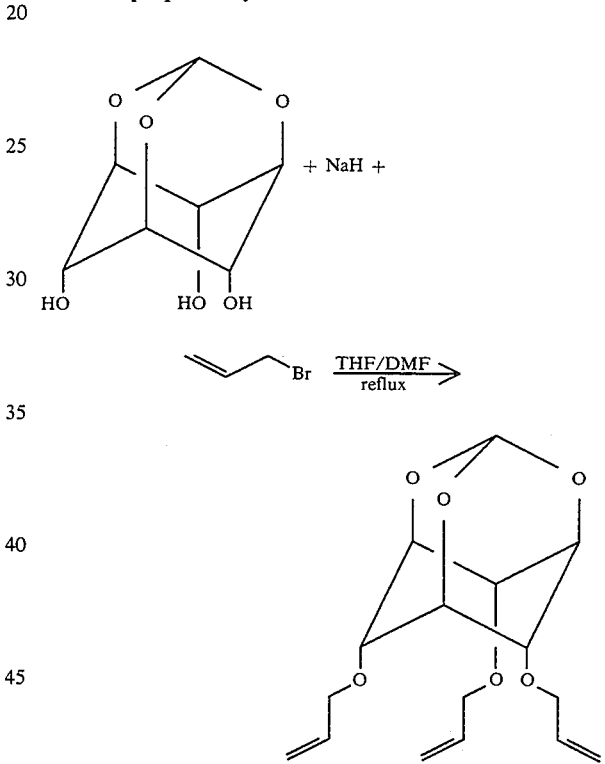

The triol (190 mg, 1.0 mmol) was dissolved in 5 ml of dry DMF, and 15 ml of anhydrous THF. Sodium hydride (60% mineral oil dispersion; 360 mg, 9.0 mmol) was then added, followed by allyl bromide (1.3 ml, 15 mmol). The mixture was then refluxed under argon for three hours, and then allowed to cool down to room temperature. The excess sodium hydride was then quenched with a small amount of crushed ice, and the excess allyl bromide and all the solvents were then removed under reduced pressure. 50 ml of water was then added to the mixture, and the product was extracted with CH$_2$Cl$_2$ three times (75 ml each). The combined organic fraction was dried over Na$_2$SO$_4$, filtered, and then concentrated in vacuo. After column chromatography, 270 mg of the product was obtained (87% yield).

MS (FAB): 333(M+Na), 311(M+H), 253, 241, 213.
HRMS: calcd =333.1295 (M+Na); found=333.1295.

IR (film): 3080cm$^{-1}$, 3015, 2960, 2864, 1854, 1646, 1458, 1426, 1401, 1357, 1320, 1288, 1264, 1170, 1133, 1075, 1003, 945, 924, 830, 757, 655.

$^1$H NMR (CDCl$_3$): 4.05 ppm (6H, ddd, J=1.4 Hz, 1.4, 5.5), 4.15 (3H, dd, J=2.7 Hz, 4.4), 4.37 (3H, dd, J=2.7 Hz, 4.4), 5.12 (3H, ddt, J=1.4 Hz, 2.0, 10.4), 5.25(3H, ddt, J=1.4 Hz, 2.0, 17.2), 5.43 (1H, s), 5.85 (3H, ddt, J=5.5 Hz, 10.4, 17.2).

$^{13}$C NMR (CDCl$_3$): 68.69ppm, 70.23, 72.03, 102.91, 116.84, 134.47.

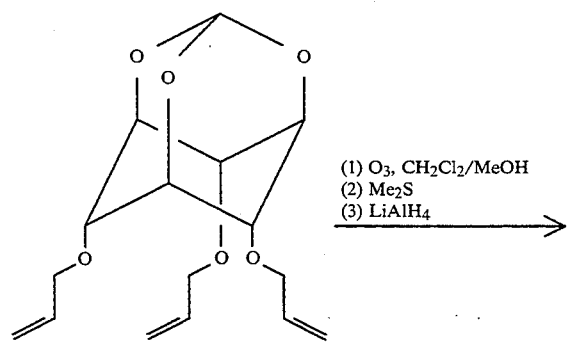

(1) O$_3$, CH$_2$Cl$_2$/MeOH
(2) Me$_2$S
(3) LiAlH$_4$

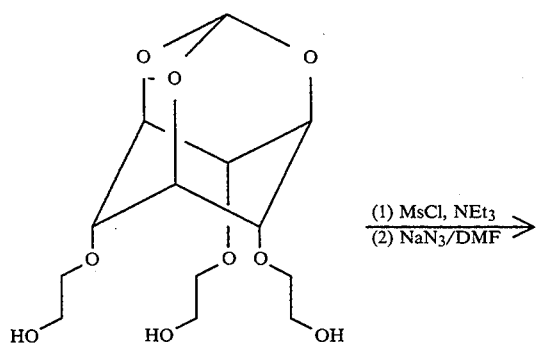

(1) MsCl, NEt$_3$
(2) NaN$_3$/DMF

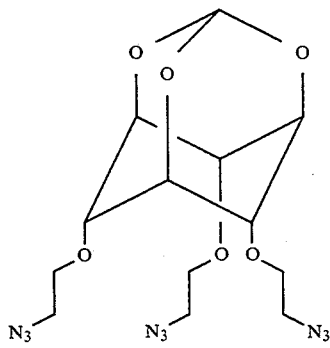

The starting material (160 mg, 0.516 mmol) was dissolved in 10 ml of CH$_2$Cl$_2$ and 20 ml of methanol. Ozone gas was then blown through the mixture at −78° C. until a blue color persisted (about 5 minutes). Nitrogen gas was then blown through the mixture for 3 minutes to remove excess ozone. 7 ml of dimethyl sulfide was then slowly added. The mixture was stirred at −78° C. for 1 hour. The excess Me$_2$S and all the solvents were then removed under reduced pressure, and the mixture was dried in vacuo. The mixture was dissolved in 30 ml of anhydrous THF, to which LiAlH$_4$(2.0 g, 0.053 mmol) was added. The mixture was stirred at room temperature overnight. The excess LiAlH$_4$ was then quenched with ethyl acetate at 0° C. Na$_2$SO$_4$.10H$_2$O salt (Glauber's salt, ~2 g) was then added and the mixture was stirred until the mixture turned white. The mixture was then filtered through celite, which was thoroughly washed with THF, and ethyl acetate. The filtrate was then concentrated and dried in vacuo. The crude triol obtained (149 mg) was used directly in the next step without purification.

To the crude product mixture obtained above in 20 ml of anhydrous CH$_2$Cl$_2$ was added triethylamine (0.97 ml, 6.96 mmol), followed by methanesulfonyl chloride (0.22 ml, 2.84 mmol). The mixture was stirred at 0° C. and allowed to warm up to room temperature over an hour. 30 ml of saturated NaHCO$_3$ solution was then added, and the product was extracted with CH$_2$Cl$_2$ three times (50 ml each). The combined organic fraction was dried over Na$_2$SO$_4$, filtered, and concentrated in vacuo. The mixture was dissolved in 15 ml of DMF to which sodium azide (2.0 g, 30.8 mmol) was added. The mixture was stirred at 70° C. overnight. The DMF was then removed under reduced pressure. 50 ml of water was added to the mixture and the triazide product was extracted with CH$_2$Cl$_2$ three times (75 ml each). The combined organic fraction was dried over Na$_2$SO$_4$, filtered and concentrated in vacuo. Purification by column chromatography gave 84 mg of the triazide (41% over 4 steps).

MS (FAB): m/z=420(M+Na), 333, 307.
HRMS: calcd=420.1356 (M+Na); found=420.1340.
IR (film): 2926cm$^{-1}$, 2867, 2102, 1440, 1283, 1167, 1134, 1092, 1045, 1000, 947, 884, 836, 637, 600.

$^1$H NMR (CDCl$_3$): 3.33 ppm (6H, t, J=3.8 Hz), 3.72 (6H, t, J=3.8 Hz), 4.23 (3H, broad), 4.47 (3H, broad), 5.48 (1H, s).

$^{13}$C NMR (CDCl$_3$): 50.97 ppm, 68.14, 68.36, 73.48, 102.96.

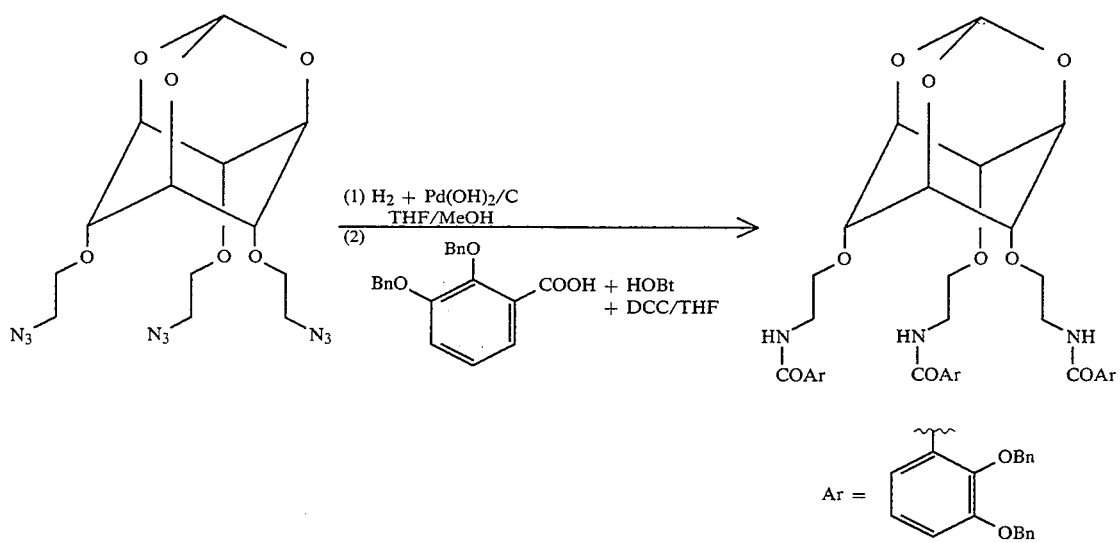

The triazide obtained (66.9 mg, 0.169 mmol) was dissolved in 5 ml of THF and 10 ml of MeOH. Pearlman's catalyst (35 mg) was then added, and the mixture was stirred under a hydrogen atmosphere (balloon) overnight. The mixture was filtered through celite, which was thoroughly washed with methanol. The filtrate was concentrated, and dried in vacuo to give 62.1 mg of crude triamine, which was used in the next step directly.

To the triamine obtained above in 10 ml of anhydrous THF was added the O-benzylated 2,3-dihydroxybenzoic acid (293 mg, 0.877 mmol), HOBt (118 mg, 0.873 mmol) and DCC (181 mg, 0.877 mmol). The mixture was then stirred under argon overnight. The THF was then removed under reduced pressure, and the product was then taken up into cold ether solution. The urea formed in the reaction was filtered off with thorough rinsing with more cold ether. The filtrate was concentrated in vacuo. After column chromatography, 195 mg of product was obtained (91% yield over two steps). MS (FAB): m/z=1290(M+Na).

HRMS: calcd=1290.4939 (M+Na); found=1290.4979.
IR (film): 3382 cm$^{-1}$, 3064, 3032, 2930, 2870, 1656, 1576, 1527, 1498, 1454, 1373, 1309, 1265, 1214, 1168, 1132, 1086, 1027, 1004, 955, 914, 853, 807, 754, 698.
UV (CH$_2$Cl$_2$): $\lambda_{max}$ 292 nm ($\epsilon$7,260), 230 (37,700).
$^1$H NMR (CDCl$_3$): 3.20 ppm (12H, broad), 3.82 (3H, dd, J=2.9 Hz, 4.0), 3.99 (3H, dd, J=2.9 Hz, 4.0), 4.95 (6H, s), 5.02 (6H, s), 5.35 (1H, s), 6.97–7.78 (39H, m).
$^{13}$C NMR (CDCl$_3$): 39.25 ppm, 67.18, 67.86, 71.05, 72.65, 76.12, 102.77, 116.51, 122.62, 124.27, 127.48, 128.04, 128.39, 128.44, 128.51, 136.42, 136.59, 146.38, 151.71, 165.51.

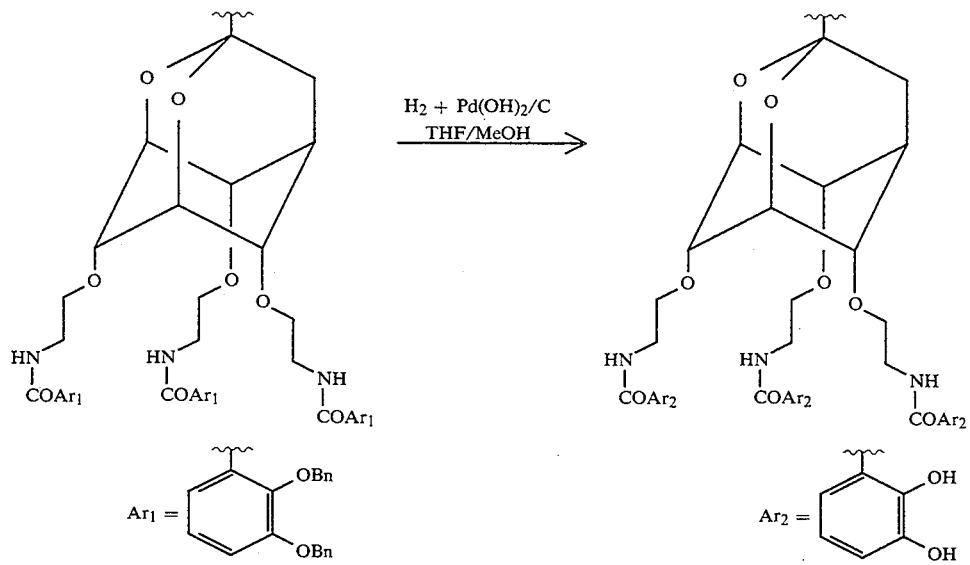

The benzylated compound (68.08 mg, 0.0537 mmol) was dissolved in 5 ml of THF and 10 ml of MeOH. Pearlman's catalyst (30 mg) was then added, and the mixture was stirred under a hydrogen atmosphere (balloon) overnight. The mixture was filtered through a piece of tightly packed cotton wool, which was thoroughly washed with methanol. The filtrate was concentrated, and dried in vacuo to give 37.11 mg of the deprotected product (95% yield).

MS (FAB): m/z=750 (M+Na), 623, 493, 403.
HRMS: calcd=750.2122 (M+Na); found=750.2121.
IR (film): 3360cm$^{-1}$, 2977 2938 2878 1641 1595 1547 1487, 1459, 1332, 1270, 1178, 1122, 1072, 1008, 892, 858, 775, 743, 623, 600.
UV (CH$_3$OH): $\lambda_{max}$ 312 nm ($\epsilon$13,300), 248 (31,300), 208 (91,700).
$^1$H NMR (CD$_3$OD): 3.38 ppm (6H, t, J=5.5 Hz), 3.66 (6H, t, J=5.5 Hz), 4.21 (3H, dd, J=2.7 Hz, 3.7), 4.48 (3H, dd, J=2.7 Hz, 3.7), 5.42 (1H, s), 6.59 (3H, dd, J=7.8 Hz, 8), 6.82 (3H, dd, J=0.7 Hz, 7.8), 7.08 (3H, dd, J=0.7 Hz, 8).
$^{13}$C NMR (CD$_3$OD): 40.29 ppm, 68.76, 69.72, 74.78, 104.28, 116.71, 118.81, 119.68, 119.75, 147.33, 150.18, 171.43.

EXAMPLE 4: Synthesis of 10-R

10-R was prepared by the reactions set forth below:

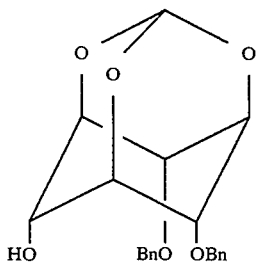 + NaH + BnBr $\xrightarrow{\text{THF}}$ reflux

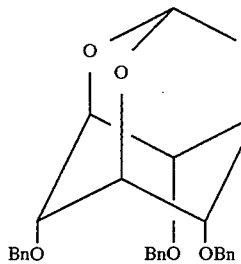

The dibenzylated compound (1.39 g, 3.76 mmol), as prepared according to the literature method (H. W.; Kishi, Y. *J. Org. Chem.*, 50, 4402 [1985], hereby incorporated by reference), was dissolved in 40 ml of anhydrous THF. Sodium hydride (60% mineral oil dispersion; 300 mg, 7.5 mmol) was then added, followed by benzyl bromide (1.5 ml, 12.6 mmol). The mixture was then refluxed overnight under argon, and was then allowed to cool down to room temperature. The excess NaH was quenched with a small amount of crushed ice, and the THF was removed under reduced pressure. 70 ml of water was then added, and the product was extracted with CH$_2$Cl$_2$ three times (100 ml each). The combined organic fraction was dried over Na$_2$SO$_4$, filtered, and concentrated in vacuo. After column chromatography, 1.62 g of product was obtained (94% yield).
MP (CH$_2$Cl$_2$/hexane): 118°–120° C.
MS (FAB): m/z=483(M+Na), 329, 307.
HRMS: calcd=483.1784 (M+Na); found=483.1756.
IR (film): 3087cm$^{-1}$, 3062, 3031, 3006, 2982, 2958, 2869, 2250, 1951, 1881, 1817, 1758, 1700, 1604, 1587, 1498, 1453, 1408, 1388, 1369, 1361, 1320, 1284, 1231, 1214, 1166, 1132, 1121, 1074, 1021, 1004, 956, 941, 911, 845, 821, 761, 740, 699, 649, 635, 611.

UV (CH$_2$Cl$_2$): $\lambda_{max}$ 262 nm ($\epsilon$450), 257 (550), 251 (420), 245 (280), 239 (247), 226 (740).
$^1$H NMR (CDCl$_3$): 4.48 ppm (3H, broad), 4.69 (6H, s), 4.70 (3H, broad), 5.70 (1H, s), 7.24–7.34 (15H, m).
$^{13}$C NMR (CDCl$_3$): 68.35 ppm, 70.93, 72.56, 102.96, 127.07, 127.51, 127.82, 137.76.

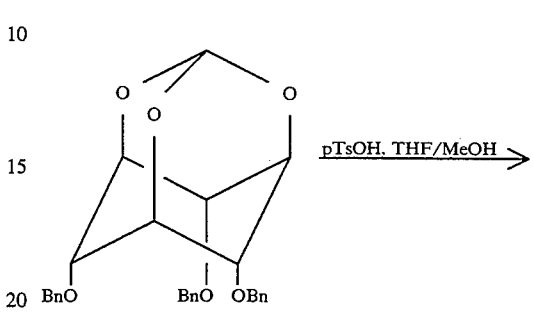

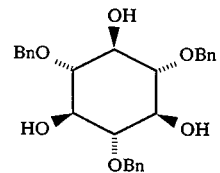

The starting material (1.19 g, 2.59 mmol) was dissolved in 5 ml of THF and 20 ml of MeOH, to which pTsOH. H$_2$O (100 mg, 0.526 mmol) was added. The mixture was stirred at room temperature for three hours. Triethylamine (1 ml, 7.17 mmol) was then added, and all the solvents were removed under reduced pressure. After column chromatography, 1.16 g of product was obtained (100% yield).
MP (CH$_2$Cl$_2$/hexane): 168°–170° C.
MS (FAB): m/z=473 (M+Na), 329.
HRMS: calcd=473.1940 (M+Na); found=473.1945.
IR (film): 3562cm$^{-1}$, 3405, 2886, 1497, 1454, 1361, 1275, 1216, 1100, 1061, 1011, 905, 740, 699, 623.
UV (CH$_2$Cl$_2$): $\lambda_{max}$ 270 nm ($\epsilon$3,790), 262 (3,870), 256 (3,320), 250 (2,530), 245 (1,660), 240 (1,180).
$^1$H NMR (CDCl$_3$): 2.61 ppm (3H, d, J=1.85 Hz), 3.31 (3H, t, J=9.39 Hz), 3.59 (3H, dt, J=1.85 Hz, 9.39), 4.87 (6H, s), 7.29–7.38 (15H, m).
$^{13}$C NMR (CDCl$_3$): 74.15 ppm, 74.89, 82.05, 127.89, 127.98, 128.57, 138.49.

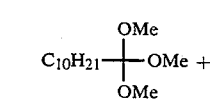 +

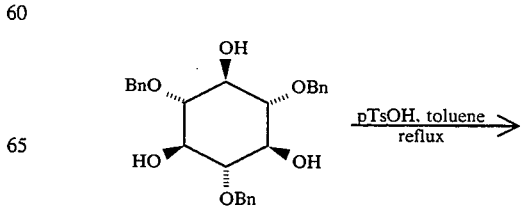

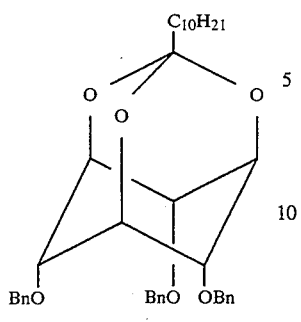
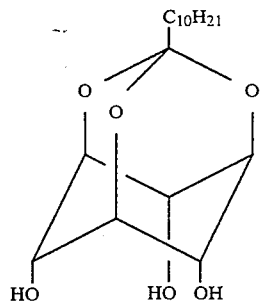

To the triol (15.0 mg, 0.033 mmol) in 3 ml of anhydrous toluene was added the trimethyl orthoester (prepared by using a slightly modified procedure of the 8 mg, 0.033 mmol), and toluenesulfonic acid (0.64 mg, 0.004 mmol). The mixture was refluxed for five hours, after which the same amount of trimethyl orthoester and toluenesulfonic acid were added. The same process was repeated, with continuous reflux of the reaction mixture, for about 24 hours, until tlc of the reaction mixture showed the desired product as the predominant species. The reaction mixture was then cooled down to room temperature, and 1 ml of triethylamine was added to neutralize the acid. All the toluene and triethylamine were then removed under reduced pressure. After purification by preparative tlc, 14.7 mg of the desired product was obtained (73% yield).

MS (FAB): m/z =601 (M+H), 493, 403, 253.
HRMS: calcd=601.3529 (M+H); found=601.3521.
IR (film): 3088 cm$^{-1}$, 3063, 3031, 2955, 2924, 2853, 1950, 1606, 1498, 1455, 1405, 1367, 1331, 1259, 1209, 1155, 1131, 1096, 1028, 994, 965, 944, 910, 735, 698, 612.
UV (CH$_2$Cl$_2$): $\lambda_{max}$ 263 nm ($\epsilon$610), 257 (750), 251 (600), 245 (440), 240 (380), 226 (580).
$^1$H NMR (CDCl$_3$): 0.80 ppm (3H, t, J=6.9 Hz), 1.15–1.25 (14H, broad), 1.40 (2H, m), 1.63 (2H, m), 4.24 (3H, dd, J=2.8 Hz, 3.9), 4.48 (3H, dd, J=2.8 Hz, 3.9), 4.51 (6H, s), 7.03–7.14 (15H, m).
$^{13}$C NMR (CDCl$_3$): 14.01 ppm, 22.56, 22.91, 29.19, 29.33, 29.36, 29.41, 29.47, 31.79, 36.87, 68.46, 71.08, 72.83, 110.01, 127.13, 127.61, 127.91, 137.95.

The triol (205.6 mg, 0.343 mmol), as prepared using the procedure above, was dissolved in 5 ml of THF and 20 ml of methanol Pearlman's catalyst (70 mg) was then added, and the mixture was stirred under a hydrogen atmosphere (balloon) for three hours. The mixture was then filtered through celite, with thorough rinsing with methanol. The filtrate was concentrated in vacuo to give 107.4 mg of product (95% yield).

MP (CHCl$_3$): 167°–170° C.
MS (FAB): m/z=331 (M+H), 261, 239, 217, 195.
HRMS: calcd=331.2120 (M+H); found=331.2110.
IR (film): 3393 cm$^{-1}$, 3204, 2954, 2921, 2853, 1470, 1384, 1318, 1261, 1088, 1063, 1012, 988, 965, 931, 887, 838, 709.
$^1$H NMR (CD$_3$OD): 0.81 ppm (3H, t, J=7.0 Hz), 1.15–1.25 (14H, broad), 1.31 (2H, m), 1.48 (2H, m), 4.11 (3H, dd, J=3.1 Hz, 4.8), 4.25 (3H, dd, J=3.1 Hz, 4.8).
$^{13}$C NMR (CD$_3$OD): 14.38 ppm, 23.69, 23.98, 30.41, 30.48, 30.54, 30.59, 30.66, 33.03, 37.87, 68.49, 72.78, 110.05.

Using the same procedures as described in Example 1 above, the product thus obtained was successfully converted to 10-R ($\alpha_D$−8.1°).

EXAMPLE 5: Synthesis of 10-S

10-S was obtained by following the same procedures set forth in Example 4 except that Corey's (R)-CBS reagent was used instead.

EXAMPLE 6: Synthesis of 11-S

The analogues with alkyl side chains were synthesized by O-alkylation with a properly functionalized tosylate, followed with necessary manipulation of the side chains thus introduced.

The synthesis of the methyl analogue 118 according to the scheme set forth below is representative:

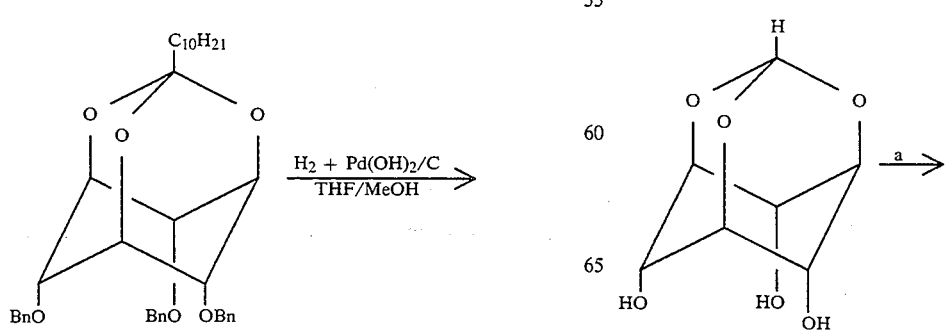

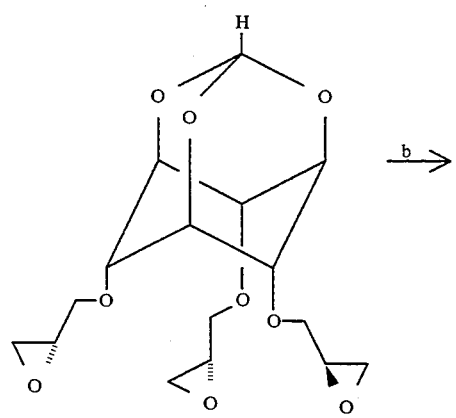

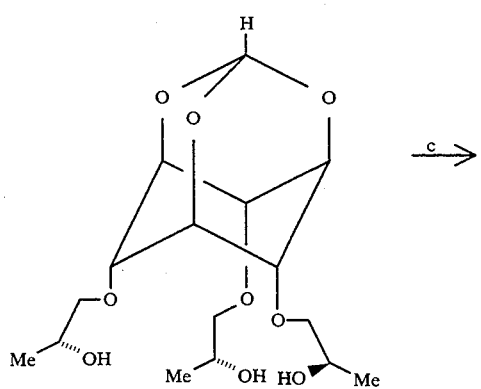

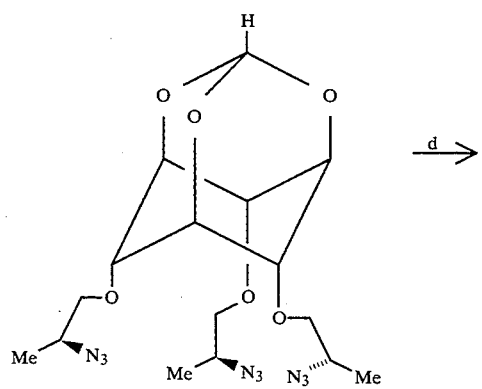

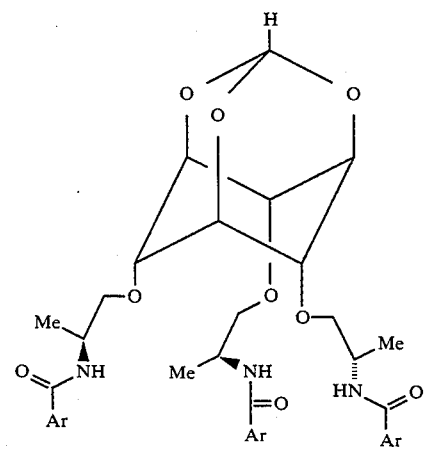

-continued

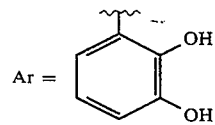

Reagents and Reaction Conditions:

Step a: (2R)—(—)—Glycidyl tosylate/NaH/DMF/room temperature.

Step b: LiAlH$_4$/TAF/−78° C to room temperature.

Step c: (1). MsCl/NEt$_3$/CH$_2$Cl$_2$/room temperature; and (2). n—Bu$_4$NN$_3$/toluene/80° C.

Step d: (1). H$_2$ (1 atm)/Pd(OH)$_2$ on C/THF-MeOH/room temperature; (2). O-dibenzyl 2,3-dihydroxybenzoic acid/HOBt/DCC/THF; and (3). H$_2$ (1 atm)/Pd(OH)$_2$ on C/THF-MeOH/room temperature.

EXAMPLE 7: Synthesis of 11-R

11-R was obtained by following the same procedures set forth in Example 6 except that (2S)—(+)—glycidyl tosylate was used in Step a.

EXAMPLE 8: Synthesis of 12-R

12-R, an enterobactin analogue with longer side chains (structure shown below), is synthesized by O-alkylation with (S)-RCH(OSiMe$_2$Bu-t)(CH$_2$)$_3$OTs, (R)-RCH(N$_3$)(CH$_2$)$_3$OTs, or RC(=CH$_2$)(CH$_2$)$_3$OTs with ozonolysis and Corey's CBS reduction, followed by functional group transformations outlined above.

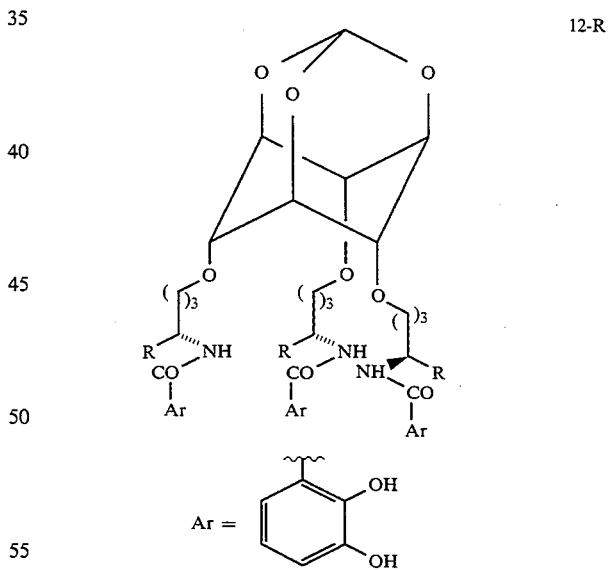

EXAMPLE 9: Synthesis of 12-S

12-S, the enantiomer of 12-R, can be prepared following the procedures described in Example 8 except that enantiomeric reagents are used instead.

EXAMPLE 10: Synthesis of 13

13 is polystyrene to which at least one or more enterobactin analogs are linked via an ether functionality, and can be readily prepared by O-alkylation and deprotection as shown below:

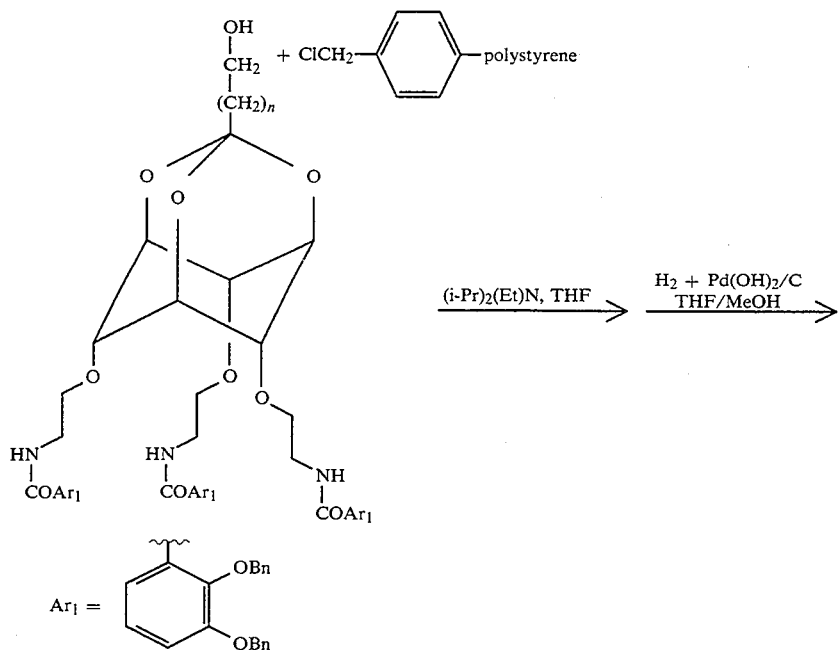

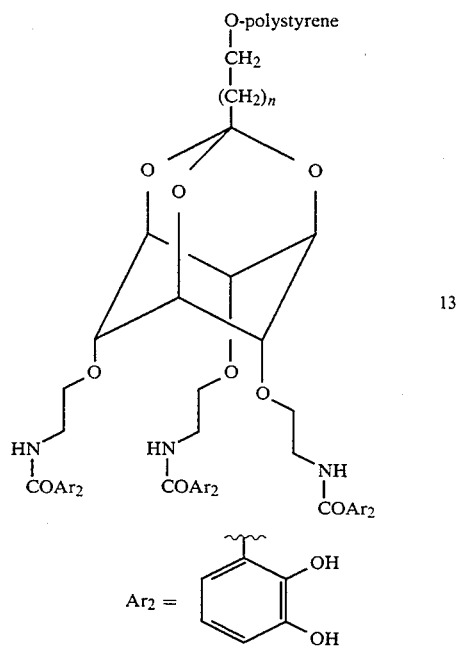

13

EXAMPLE 11: Determination of Metal Ion-Binding and Other Properties of Enterobactin Analogs Both 6-R and 6-S bind ferric ions to give deep red complexes ($\lambda_{max}$ 495 nm, $\epsilon \sim 3,600$ at pH 7). As expected, the CD spectra (FIG. 1) of their ferric complexes 6-$R_{Fe}$ and 6-$S_{Fe}$ were found to be mirror images. Like the ferric complex of enterobactin, 6-$R_{Fe}$ and 6-$S_{Fe}$ showed CD bands in the ligand-to-metal charge transfer region ($\sim$540 nm), indicating that the ligand chirality of 6-S and 6-R induced a preference for the right-handed ($\Delta$) metal complex over the left-handed one ($\Lambda$) or vice versa. Comparing the signs of the CD bands of 6-$R_{Fe}$ and 6-$S_{Fe}$ at $\sim$540 nm with the literature data allowed the assignment of $\Delta$-cis to 6-$S_{Fe}$ and $\Lambda$-cis to 6-$R_{Fe}$. However, the ratio of $\Delta$:$\Lambda$ of the complexes cannot be deduced from CD spectroscopy alone. Proton NMR spectra of the diamagnetic Ga(III)-complexes of enterobactin and its analogs were shown to be useful for determining the ratio of $\Delta$:$\Lambda$. Thus, the Ga(III)-complexes of 6-R and 6-S were prepared and subjected to variable temperature NMR studies. Over a wide range of temperatures (230° to 333° K.), $_1$H NMR of the Ga(III)-complexes showed only one set of well-defined signals, showing that the complexes were exclusively $\Delta$-cis in the case of 6-$S_{Ga}$ and exclusively $\Lambda$-cis in the case of 6-$R_{Ga}$. With the similarities of the coordination chemistry of Fe(III) and Ga(III), the same assignment can be made for the ferric complexes of 6-R and 6-S.

The stability constants $K_f$ for both 6-$S_{Fe}$ and 6-$R_{Fe}$ were measured. For the purpose of comparison, the achiral analog 7, which differs from 6 only in lacking the phenyl groups, was synthesized. With a small modification of the method established by Raymond (*J. Am. Chem. Soc.*, 101:6097 [1979], hereby incorporated by reference), the Kf values were estimated as follows. The enterobactin analog i (structure shown below) was synthesized. The ferric complex of i was determined to have Kf=1048.8. EDTA competition experiments on both 6 and i were then performed. Assuming the overall pKa of the six catecholic protons to be 58.5 and measuring the decrease in $\epsilon$ of the ferric complex at 495 nm in the presence of $5 \times 10^4$M to $10^{-2}$M EDTA, the $K_f$ value of $6_{Fe}$ was estimated to be approximately one order of magnitude lower than the ferric complex of i. The $K_f$ values for other analogs were estimated likewise. As expected, the chemical behavior of 7 towards ferric ions was parallel to that of 6. Yet, the stability constant $K_f$ for 7 was found to be about two orders of magnitude lower than that of 6.

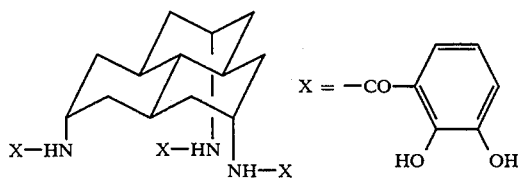

i

We attribute this difference primarily to an entropic factor; with the small scyllo-inositol as the platform, the relatively bulky phenyl groups point outward to minimize steric congestion, and the three catechol groups are pre-organized in such a way that the entropy lost upon binding with Fe(III) is less for 6 than the relatively flexible 7. It is intriguing to note that the stability constant $K_f$ for 6 was estimated to be only one order of magnitude lower than $K_f$ for enterobactin itself.

As anticipated, the analog 10-R was found to be much more lipophilic than the corresponding 6. Like 6-R, 10-R was found to chelate ferric ions and give a deep-red complex ($\lambda_{max}$ 495 nm, $\epsilon \sim 4,000$ at pH 7), with a $K_f$ similar to that of 6-$R_{Fe}$. The CD spectrum of 10-$R_{Fe}$ was virtually identical to that of 6-$R_{Fe}$. The $^1$H NMR spectrum of 10-$R_{Ga}$ exhibited only one set of well-defined signals, suggesting that 10-R also bound Ga(III), and thus Fe(III), exclusively in the $\Lambda$-fashion. The most exciting observation was that 10-$R_{Fe}$ showed excellent solubility in organic solvents; upon partitioning between water and EtOAc or CHCl$_3$, 10-$R_{Fe}$ appeared only in the organic layer, whereas 6-$R_{Fe}$ appeared only in the aqueous layer.

Without further elaboration, it is believed that one skilled in the art can, based on the above working examples and other descriptions herein, utilize the present invention to its fullest extent.

For example, the enterobactin analog (hexabenzylated on the catechol moieties) synthesized from scyllo-inositol mono-orthoformate can be hydrolyzed with pTsOH in methanol, followed by reactions with Br—CH$_2$—(CH$_2$)n—C(OMe)$_3$, pTsOH in refluxing xylene to give a different enterobactin analog (hexabenzylated on the catechol moieties) with a different orthoester moiety bearing a —(CH$_2$)n—CH$_2$Br chain. The bromide can then be displaced by various nucleophiles to give many more enterobactin analogues.

More specifically, (1) Br can be displaced by acetate, and after cleavage of the acetate, the analog with a terminal —CH$_2$OH group is formed; (2) Br can be displaced by the enolate of benzyl acetate, and after hydrogenolysis, the analog with a terminal —CH$_2$COOH group is formed; and (3) Br can be displaced by azide and after hydrogenation or treatment with PPh$_3$, H$_2$O, the analog with a terminal —CH$_2$NH$_2$ is formed; (4) Br can also be displaced by various amines to form an analog with a terminal amino group.

Furthermore, one can attach the analogs to different types of solid supports (e.g., polymers). For example, when the analog (hexabenzylated on the catechol moieties) with a terminal —CH$_2$OH reacts with a polystyrene support which has terminal benzyl chloride groups in the presence of a base, the ligand then becomes attached to the solid support via an ether functionality. As another example, when the analog (hexabenzylated on the catechol moieties) with a terminal —CH$_2$Br reacts with a polystyrene support which has terminal benzyl alcohol groups in the presence of a base, the ligand can then be attached to the solid support via an ether functionality. In addition, when the analog (hexabenzylated on the catechol moieties) with a terminal —CH$_2$NH$_2$ reacts with a polyacrylamide resin with terminal methyl ester groups, the ligand can then be attached to the solid support via amide bonds. Moreover, the analogs with terminal carboxylic acid groups or amino groups can also be electrostatically anchored to cationic or anionic ion-exchange resins respectively.

OTHER EMBODIMENTS

From the above description, one skilled in the art can easily ascertain the essential characteristics of the present invention, and without departing from the spirit and scope thereof, can make various changes and modifications of the invention to adapt it to various usages and conditions. Thus, other embodiments are also within the claims.

For example, while phenyl is assigned to X$_1$, X$_2$, X$_3$ and Y in formula (I), properly substituted phenyl is also contemplated. By the same token, a properly functionalized alkyl group (e.g., alkenyl) can also be assigned to X$_1$, X$_2$, X$_3$ or Y, although only C$_{1-20}$ alkyl is expressly stated.

What is claimed is:

1. A compound of the following formula:

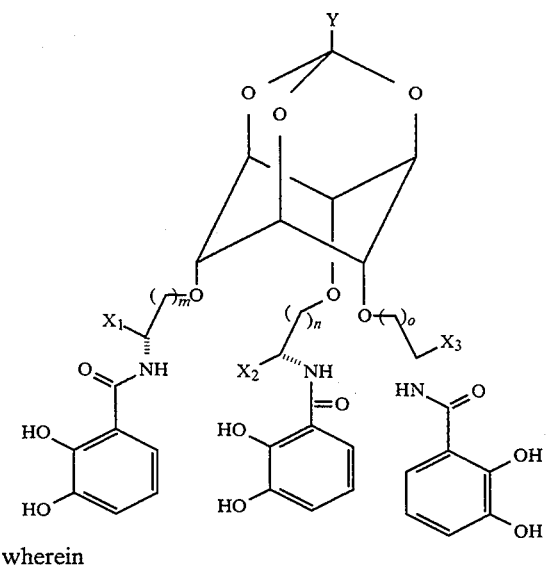

wherein each $X_1$, $X_2$ and $X_3$, independently, is H, $C_{1-20}$ alkyl, phenyl, naphthyl, $C_{7-20}$ aralkyl, or $C_{7-20}$ alkaryl;

Y is H, $C_{1-20}$ alkyl, phenyl, naphthyl; $C_{7-20}$ aralkyl, $C_{7-20}$ alkaryl; $-(C_pH_{2p})-CH_2OH$, $-C_pH_{2p})-COOH$ or its salt, $-(C_pH_{2p})-NR_1.R_2$ or its salt, or $-(C_pH_{2p})-N^+R_1.R_2.R_3$; in which p is 1–20 and each $R_1$, $R_2$ and $R_3$, independently, is H or $C_{1-5}$ alkyl; and m, n and o, independently, is 1–6; or the enantiomer thereof.

2. The compound of claim 1, wherein each $X_1$, $X_2$ and $X_3$, independently, is H, methyl, or phenyl.

3. The compound of claim 1, wherein Y is H, $-CH.(CH_3)_2$, $-C(CH_3)_3$, $-(CH_2)_p-CH_2OH$, $-(CH_2)_p-COOH$ or its salt $-(CH_2)_p-NR_1.R_2$ or its salt, $-(CH_2)_p-N^+R_1.R_2.R_3$; or $-(CH_2)_q-CH_3$, in which each p and q, independently, is 1–10.

4. The compound of claim 3, wherein each $X_1$, $X_2$ and $X_3$, independently, is H, methyl, or phenyl.

5. The compound of claim 1, wherein m, n and o are identical.

6. The compound of claim 5, wherein each m, n and o, independently, is 1.

7. The compound of claim 4, wherein m, n and o are identical.

8. The compound of claim 7, wherein each m, n and o, independently, is 1.

9. The compound of claim 1, wherein $X_1$, $X_2$ and $X_3$ are identical.

10. The compound of claim 4, wherein $X_1$, $X_2$ and $X_3$ are identical.

11. The compound of claim 6, wherein $X_1$, $X_2$ and $X_3$ are identical.

12. The compound of claim 8, wherein $X_1$, $X_2$ and $X_3$ are identical.

13. The compound of claim 1, wherein each of the hydroxyl groups of the catechol moieties is blocked by an alcohol protecting group.

14. The compound of claim 4, wherein each of the hydroxyl groups of the catechol moieties is blocked by an alcohol protecting group.

15. The compound of claim 6, wherein each of the hydroxyl groups of the catechol moieties is blocked by an alcohol protecting group.

16. The compound of claim 8, wherein each of the hydroxyl groups of the catechol moieties is blocked by an alcohol protecting group.

* * * * *